United States Patent
Madabhushi et al.

(10) Patent No.: US 12,008,747 B2
(45) Date of Patent: Jun. 11, 2024

(54) POPULATION-SPECIFIC PREDICTION OF PROSTATE CANCER RECURRENCE BASED ON STROMAL MORPHOLOGY FEATURES

(71) Applicant: Case Western Reserve University, Cleveland, OH (US)

(72) Inventors: Anant Madabhushi, Shaker Heights, OH (US); Hersh Bhargava, San Francisco, CA (US); Patrick Leo, Honeoye Falls, NY (US); Priti Lal, Ellicott City, MD (US)

(73) Assignee: Case Western Reserve University, Cleveland, OH (US)

( * ) Notice: Subject to any disclaimer, the term of this patent is extended or adjusted under 35 U.S.C. 154(b) by 834 days.

(21) Appl. No.: 16/886,966

(22) Filed: May 29, 2020

(65) Prior Publication Data
US 2021/0035694 A1    Feb. 4, 2021

Related U.S. Application Data

(60) Provisional application No. 62/879,711, filed on Jul. 29, 2019.

(51) Int. Cl.
*G16H 50/30*    (2018.01)
*G06N 7/01*    (2023.01)
(Continued)

(52) U.S. Cl.
CPC .......... *G06T 7/0012* (2013.01); *G06N 7/01* (2023.01); *G06N 20/00* (2019.01); *G06T 7/11* (2017.01);
(Continued)

(58) Field of Classification Search
CPC .............. G06T 7/0012; G06T 7/11; G06T 2207/20076; G06T 2207/20081;
(Continued)

(56) References Cited

U.S. PATENT DOCUMENTS

| 2003/0073096 A1* | 4/2003 | Bao ................ G01N 33/57434 |
| | | 435/6.15 |
| 2008/0031521 A1* | 2/2008 | Can ..................... G06V 20/698 |
| | | 382/173 |

(Continued)

FOREIGN PATENT DOCUMENTS

| CA | 2585561 C * | 7/2018 | ........... C12Q 1/6886 |
| WO | WO-2019108888 A1 * | 6/2019 | ........... G06K 9/0014 |
| WO | WO-2019110583 A1 * | 6/2019 | ......... G06K 9/00147 |

OTHER PUBLICATIONS

Hersh Kumar Bhargava "Computer-extracted stromal features of African-Americans versus Caucasians from H&E slides and impact on prognosis of biochemical recurrence" journal of Clinical Oncology (Year: 2018).*

(Continued)

*Primary Examiner* — Mekonen T Bekele
(74) *Attorney, Agent, or Firm* — Eschweiler & Potashnik, LLC

(57) ABSTRACT

Embodiments discussed herein facilitate determination of one of a probability of prostate cancer recurrence-free survival or a risk factor associated with prostate cancer based on intra-tumor stromal morphology. Example embodiments can perform operations comprising: accessing a digitized histological image of a prostate of a patient, wherein the histological image comprises a region of interest associated with prostate cancer; identifying nuclei of intratumoral stromal cells within the region of interest; extracting, for the region of interest of the digitized histological image, one or more features describing the structure of the intra-tumoral stromal cells; and generating, via a model based at least on the one or more features, one of a probability of prostate cancer recurrence-free survival or a risk score associated with prostate cancer for the patient based at least on the extracted one or more features.

26 Claims, 17 Drawing Sheets

(51) Int. Cl.
*G06N 20/00* (2019.01)
*G06T 7/00* (2017.01)
*G06T 7/11* (2017.01)
*G06V 10/778* (2022.01)
*G16H 30/40* (2018.01)

(52) U.S. Cl.
CPC ......... *G06V 10/7796* (2022.01); *G16H 30/40* (2018.01); *G16H 50/30* (2018.01); *G06T 2207/20076* (2013.01); *G06T 2207/20081* (2013.01); *G06T 2207/30081* (2013.01)

(58) Field of Classification Search
CPC . G06T 2207/30081; G06T 2207/20084; G06T 2207/30024; G06N 7/01; G06N 20/00; G06N 3/045; G06N 5/01; G06N 20/20; G06F 18/2113; G16H 50/20
See application file for complete search history.

(56) References Cited

U.S. PATENT DOCUMENTS

2014/0303034 A1* 10/2014 Gascoyne ............... G16B 25/10
506/9
2017/0270666 A1* 9/2017 Barnes ............ G01N 33/57415

OTHER PUBLICATIONS

Jin Tae Kwak, "Correlation of magnetic resonance imaging with digital histopathology in prostate" Int J CARS (2016) 1 (Year: 2015).*

Jin Tae Kwak, "Correlation of magnetic resonance imaging with digital histopathology in prostate" in view of Barnes et al., (Year: 2015).*

Beck et al. "Systematic Analysis of Breast Cancer Morphology Uncovers Stromal Features Associated with Survival." Science Translational Medicine, vol. 3 Issue 108 108ra113, published on Nov. 9, 2011.

Haeggloef et al. "TMPRSS2-ERG Expression Predicts Prostate Cancer Survival and Associates with Stromal Biomarkers." PLoS One 9(2): e86824. doi:10.1371/journal.pone.0086824 Published Feb. 5, 2014.

Lee et al. "Nuclear Shape and Architecture in Benign Fields Predict Biochemical Recurrence in Prostate Cancer Patients Following Radical Prostatectomy: Preliminary Findings." Eur Urol Focus. Oct. 2017 ; 3(4-5): 457-466. doi:10.1016/j.euf.2016.05.009. Published Oct. 2017.

Bhargava et al. "Computer-Extracted Stromal Features of African-Americans vs. Caucasians From H&E Slides and Impact on Prognosis of Biochemical Recurrence." Presented at ASCO Annual Meeting, Jun. 1-Jun. 5, 2018, Chicago, IL, USA.

* cited by examiner

| Variable | Subvariables | Fraction (%) or mean (STD) |
|---|---|---|
| Number of Patients (%) | Total<br>Training<br>Validation | 334<br>127 (38%)<br>207 (62%) |
| Mean (std. dev.) of age in years | | 59.54 (7.15) |
| Race | African-American (AA)<br>Caucasian-American (CA) | 170 (51%)<br>164 (49%) |
| Mean (std. dev.) preoperative PSA in ng/mL | Recurrence<br>Non-Recurrence | 10.95 (11.37)<br>7.92 (11.52) |
| Pathological Gleason Grade (number of patients) | 6 or less<br>7<br>8 or greater | 109 (33%)<br>197 (59%)<br>28 (8%) |
| Pathological Stage (number of patients) | T2x<br>T3x<br>Data not available (either T2x or T3x) | 170 (51%)<br>94 (28%)<br>70 (21%) |
| Mean (std. dev.) days to event | Recurrence<br>Last follow-up (Non-Recurrence) | 1063 (1120)<br>1717 (1411) |

FIG. 7

| Parameter | Dataset $V_{1,AA}$ | | Dataset $V_{2,AA}$ | |
|---|---|---|---|---|
| | HR (95% CI) | P Value | HR (95% CI) | P Value |
| AAstroENC Score | 2.80 (1.15 - 6.85) | 0.024 | 2.36 (1.38 - 4.06) | 0.002 |
| Age at time of surgery | 0.31 (0.11 - 0.85) | 0.023 | 0.79 (0.34 - 1.84) | 0.592 |
| Pathological Gleason Score (primary + secondary) | 1.42 (0.55 - 3.66) | 0.464 | 1.33 (0.46 - 3.86) | 0.595 |
| Preoperative PSA Value | 2.16 (0.95 - 4.93) | 0.067 | 1.70 (0.78 - 3.73) | 0.181 |
| Presence of SVI | 2.56 (1.07 - 6.12) | 0.034 | 2.49 (1.16 - 5.31) | 0.019 |
| Presence of ECE | 0.75 (0.23 - 2.48) | 0.635 | 0.85 (0.25 - 2.93) | 0.795 |
| Positive Surgical Margins | 0.63 (0.27 - 1.47) | 0.285 | 1.18 (0.59 - 2.36) | 0.649 |

FIG. 8

|  | T$_{AA}$ Training | | T$_{CA}$ Training | | T$_{AA+CA}$ Training | |
|---|---|---|---|---|---|---|
|  | Random Forest | Elastic Net Cox | Random Forest | Elastic Net Cox | Random Forest | Elastic Net Cox |
| V1$_{AA}$ | AUC: 0.85<br>HR: 3.03 (95%<br>CI: 0.812 - 11.3)<br>p: 0.024 | AUC: 0.87<br>HR: 4.71 (95%<br>CI: 1.65 - 13.4)<br>p: 0.0027 | AUC: 0.39<br>HR: 1.62 (0.569<br>- 4.63)<br>p: 0.62 | AUC: 0.48<br>HR: 1.74 (0.58 -<br>5.23)<br>p: 0.323 | AUC: 0.78<br>HR: 1.96 (0.65 -<br>5.85)<br>p: 0.14 | AUC: 0.55<br>HR: 0.83 (0.09 -<br>7.50)<br>p: 0.86 |
| V2$_{AA}$ | AUC: 0.75<br>HR: 4.51 (95%<br>CI: 0.925 - 22)<br>p: 0.013 | AUC: 0.77<br>HR: 5.70 (95%<br>CI: 1.48 - 21.9)<br>p: 0.014 | AUC: 0.60<br>HR: 1.15 (0.296<br>- 4.47)<br>p: 0.84 | AUC: 0.56<br>HR: 0.31<br>(0.0099 - 9.74)<br>p: 0.242 | AUC: 0.88<br>HR: 4.56 (1.1 -<br>18.9)<br>p: 0.018 | AUC: 0.56<br>HR: 0.61 (0.05 -<br>7.79)<br>p: 0.63 |
| V1$_{CA}$ | AUC: 0.33<br>HR: 0.466<br>(0.106 - 2.05)<br>p: 0.45 | AUC: 0.50<br>HR: 0.921<br>(0.338 - 2.51)<br>p: 0.87 | AUC: 0.56<br>HR: 0.987 (0.32<br>- 3.05)<br>p: 0.98 | AUC: 0.47<br>HR: 0.54 (0.17 -<br>1.69)<br>p: 0.22 | AUC: 0.49<br>HR: 1.01 (0.29 -<br>3.55)<br>p: 0.99 | AUC: 0.40<br>HR: 0.87 (0.29 -<br>2.58)<br>p: 0.79 |
| V2$_{CA}$ | AUC: 0.44<br>HR: 0.546 (95%<br>CI 0.183 - 1.62)<br>p: 0.33 | AUC: 0.49<br>HR: 1.74 (0.56 -<br>5.38)<br>p: 0.28 | AUC: 0.44<br>HR: 0.832<br>(0.299 - 2.32)<br>p: 0.72 | AUC: 0.49<br>HR: Infinite<br>p: 0.224 | AUC: 0.45<br>HR: 0.47 (0.16 -<br>1.37)<br>p: 0.22 | AUC: 0.46<br>HR: 1.47 (0.40 -<br>5.43)<br>p: 0.60 |
| V1$_{AA+CA}$ | AUC: 0.66<br>HR: 1.57 (0.56 -<br>4.43)<br>p: 0.31 | AUC: 0.68<br>HR: 1.84 (0.90 -<br>3.78)<br>p: 0.082 | AUC: 0.55<br>HR: 0.744<br>(0.368 - 1.51)<br>p: 0.40 | AUC: 0.46<br>HR: 0.84 (0.38 -<br>1.89)<br>p: 0.64 | AUC: 0.58<br>HR: 1.32 (0.53 -<br>3.30)<br>p: 0.51 | AUC: 0.46<br>HR: 0.61 (0.21 -<br>1.75)<br>p: 0.26 |
| V2$_{AA+CA}$ | AUC: 0.71<br>HR: 2.10 (0.83 -<br>5.32)<br>p: 0.21 | AUC: 0.61<br>HR: 2.37 (0.99 -<br>5.69)<br>p = 0.028 | AUC: 0.52<br>HR: 1.19<br>(0.593-2.38)<br>p: 0.63 | AUC: 0.54<br>HR: 1.67 (0.34 -<br>8.21)<br>p: 0.56 | AUC: 0.53<br>HR: 1.14 (0.62 -<br>2.08)<br>p: 0.68 | AUC: 0.49<br>HR: 1.06 (0.325<br>- 3.47)<br>p: 0.92 |

| Model | $V_{1,AA}$ Performance | $V_{2,AA}$ Performance |
|---|---|---|
| CAPRA-S Nomogram | AUC: 0.74<br>HR: 2.53 (0.847 - 7.53)<br>p: 0.059 | AUC: 0.70<br>HR: 2.99 (0.603 - 14.8)<br>p: 0.086 |
| Kattan Nomogram | AUC: 0.75<br>HR: 2.67 (0.826 - 8.65)<br>p: 0.045 | AUC: 0.62<br>HR: 2.20 (0.409 - 11.8)<br>p: 0.252 |
| AAstroENC Classifier | AUC: 0.87<br>HR: 4.71 (1.65 - 13.4)<br>p: 0.0027 | AUC: 0.77<br>HR: 5.70 (1.48 - 21.9)<br>p: 0.014 |

| Model | Features |
|---|---|
| AAstroML | Shape: Min / Max Fourier Descriptor 4<br>Shape: Mean Fractal Dimension<br>Shape: Median Fractal Dimension<br>Haralick: Mean Information Measure 1<br>Shape: Std. Deviation Variance Of Distance<br>Shape: Min / Max Distance Ratio |
| AAstroENC | Shape: Mean Distance Ratio<br>Shape: Mean Fractal Dimension<br>Shape: Std. Deviation Perimeter Ratio<br>Shape: Median Fractal Dimension<br>Shape: Min / Max Perimeter Ratio<br>Shape: Min / Max Fourier Descriptor 4<br>CGT: Mean Tensor Correlation<br>Sub-Graph: Number Isolated Nodes<br>Haralick: Mean Contrast Inverse Moment<br>Haralick: Mean Intensity Average |

FIG. 11

| Biomarker | Feature Name | PCC | p-value |
|---|---|---|---|
| PTEN | Shape:Mean Fourier Descriptor 4 | -0.623 | 7.56E-03 |
| RB (cyt.) | Shape:Mean Fractal Dimension | 0.606 | 4.97E-04 |
| PTEN | Shape:Std. Deviation Fourier Descriptor 3 | -0.605 | 1.01E-02 |
| RB (cyt.) | Shape:Mean Invariant Moment 2 | -0.601 | 5.59E-04 |
| PTEN | Shape:Std. Deviation Fourier Descriptor 4 | -0.598 | 1.12E-02 |
| PTEN | Shape:Std. Deviation Fourier Descriptor 8 | -0.586 | 1.34E-02 |
| PTEN | Shape:Std. Deviation Fourier Descriptor 2 | -0.585 | 1.35E-02 |
| PTEN | Shape:Std. Deviation Fourier Descriptor 10 | -0.583 | 1.40E-02 |
| PTEN | Shape:Mean Fourier Descriptor 10 | 0.580 | 1.46E-02 |
| PTEN | Shape:Std. Deviation Fourier Descriptor 9 | -0.576 | 1.54E-02 |
| PTEN | Shape:Mean Fourier Descriptor 7 | 0.571 | 1.66E-02 |
| PTEN | Shape:Mean Fourier Descriptor 8 | 0.565 | 1.81E-02 |
| ERG | Delaunay:Triangle Area Disorder | -0.557 | 5.72E-03 |
| PTEN | Shape:Mean Fourier Descriptor 1 | 0.552 | 2.15E-02 |
| PTEN | Shape:Std. Deviation Fourier Descriptor 6 | -0.549 | 2.24E-02 |
| PTEN | Shape:Std. Deviation Fourier Descriptor 1 | -0.547 | 2.29E-02 |
| PTEN | Shape:Mean Distance Ratio | -0.536 | 2.65E-02 |
| PTEN | Shape:Std. Deviation Fourier Descriptor 5 | -0.535 | 2.70E-02 |
| ERG | Voronoi:Area Disorder | -0.454 | 2.96E-02 |
| ERG | Haralick:Mean Information Measure 1 | -0.447 | 3.26E-02 |
| C-MYC | Sub-Graph:Std. Deviation Edge Length | 0.446 | 2.38E-03 |
| RB (nuc.) | Haralick:Mean Intensity Average | -0.439 | 1.06E-02 |
| ERG | Shape:Min / Max Fourier Descriptor 8 | -0.438 | 3.64E-02 |
| C-MYC | Sub-Graph:Kurtosis Edge Length | -0.422 | 4.37E-03 |
| C-MYC | Sub-Graph:Mean Edge Length | -0.419 | 4.68E-03 |
| AR | Shape:Mean Fractal Dimension | 0.414 | 4.12E-04 |
| RB (cyt.) | Arch:Disorder Of Nearest Neighbors In A 10 Pixel Radius | -0.412 | 2.64E-02 |
| AR | Shape:Mean Distance Ratio | -0.410 | 4.72E-04 |
| RB (nuc.) | Arch:Std. Deviation Nearest Neighbors In A 20 Pixel Radius | 0.404 | 1.97E-02 |

FIG. 12

| Feature class | Derived attributes |
|---|---|
| Voronoi Tessellation (12 features) | Number of nodes, number of edges, area, chord parameters |
| Delaunay Triangulation (8 features) | Side lengths, triangle geometry |
| Minimum Spanning Tree (4 features) | Number of nodes, edge length, degree, number of neighbors |
| Local Nuclear Cluster Graph (26 features) | Structure of clusters, patterning of clusters within graph |
| Nuclear Shape (100 features) | Nuclear area, perimeter, Fourier descriptors, invariant moments |
| Cell Orientation Entropy (39 features) | Contrast energy, Contrast inverse moment, Contrast average, Contrast variance, Contrast entropy, Intensity average, Intensity variance, Intensity entropy, Entropy, Energy, Correlation, 2 measures of information |
| Sub-Graph Features (26 features) | Number of nodes, number of edges, eccentricity, clustering coefficients |
| Texture Features (26 features) | Texture, edges, gradients, spots, and homogeneity of the image. Entropy, variance, and energy are calculated from the co-occurrence matrix describing how often pixels of various intensities are found near pixels of another intensity. |

FIG. 13

| Cohort | Feature Name | P Value | Haz. Ratio | BCR Mean | NR Mean | % Diff. |
|---|---|---|---|---|---|---|
| AA | Shape: Min / Max Fourier Descriptor 4 | 1.577E-05 | 4.334E-01 | -1.128 | -1.026 | 9.409 |
| AA | Shape: Mean Fractal Dimension | 2.683E-05 | 3.041 | 2.580E-01 | 2.438E-01 | 5.684 |
| AA | Shape: Median Fractal Dimension | 1.294E-04 | 2.131 | 2.309E-01 | 2.164E-01 | 6.526 |
| AA | Haralick: Mean Information Measure 1 | 1.289E-02 | 1.950 | 3.346 | 3.261 | 2.591 |
| AA | Shape: Std. Deviation Variance Of Distance | 1.456E-02 | 5.760E-01 | 1.774E-02 | 1.802E-02 | -1.592 |
| AA | Shape: Min / Max Distance Ratio | 4.507E-02 | 1.619 | 5.936E-01 | 5.955E-01 | -3.137E-01 |

FIG. 14

| Cohort | Feature Name | P Value | Haz. Ratio | BCR Mean | NR Mean | % Diff. |
|---|---|---|---|---|---|---|
| CA | Delaunay: Triangle Area Std. Deviation | 5.777E-05 | 2.030 | 3.489E+01 | 2.145E+01 | 4.774E+01 |
| CA | CGT: Std. Deviation Tensor Contrast Energy | 3.370E-04 | 1.846 | 4.631E-01 | 6.099E-03 | 1.635E+02 |
| CA | Sub-Graph: Number Isolated Nodes | 7.278E-04 | 2.401 | 3.333E-01 | 1.538E-01 | 7.368E+01 |
| CA | CGT: Std. Deviation Tensor Information Measure 1 | 7.886E-04 | 1.703 | 5.529E-03 | 1.094E-03 | 1.339E+02 |
| CA | MST: Edge Length Disorder | 1.081E-03 | 2.280 | 4.453E-01 | 4.166E-01 | 6.655 |
| CA | Delaunay: Side Length Disorder | 1.097E-03 | 2.081 | 4.658E-01 | 4.462E-01 | 4.290 |
| CA | MST: Edge Length Std. Deviation | 3.902E-03 | 1.550 | 2.323 | 1.809 | 2.490E+01 |
| CA | Shape: Mean Fourier Descriptor 2 | 7.965E-03 | 5.440E-01 | 1.668E-05 | 3.271E-05 | -6.491E+01 |
| CA | CGT: Range Tensor Information Measure 1 | 8.150E-03 | 1.639 | 6.677E-02 | 2.066E-02 | 1.056E+02 |
| CA | Voronoi: Chord Minimum / Maximum | 1.080E-02 | 5.201E-01 | 5.451E-02 | 5.853E-02 | -7.112 |
| CA | Arch: Disorder Of Distance To 3 Nearest Neighbors | 1.115E-02 | 1.827 | 3.623E-01 | 3.372E-01 | 7.151 |
| CA | Shape: Mean Invariant Moment 3 | 1.307E-02 | 5.627E-01 | 3.623E-04 | 3.965E-04 | -9.023 |
| CA | Delaunay: Side Length Minimum / Maximum | 1.535E-02 | 5.467E-01 | 6.983E-02 | 8.020E-02 | -1.382E+01 |
| CA | Voronoi: Perimeter Minimum / Maximum | 1.760E-02 | 5.664E-01 | 3.282E-03 | 3.487E-03 | -6.069 |
| CA | Shape: Min / Max Perimeter Ratio | 2.067E-02 | 1.707 | 2.228E-01 | 2.151E-01 | 3.549 |
| CA | Shape: Mean Invariant Moment 7 | 2.131E-02 | 6.458E-01 | -6.373E-10 | 9.626E-12 | 2.061E+02 |
| CA | Arch: Density Of Polygons | 2.625E-02 | 4.829E-01 | 4.563E-02 | 6.173E-02 | -3.021E+01 |
| CA | Shape: Mean Area Ratio | 2.784E-02 | 1.705 | 3.552E-01 | 3.454E-01 | 2.780 |
| CA | Sub-Graph: Std. Deviation Edge Length | 3.601E-02 | 1.460 | 6.416 | 6.304 | 1.762 |
| CA | Voronoi: Perimeter Disorder | 3.874E-02 | 1.641 | 4.578E-01 | 4.474E-01 | 2.296 |
| CA | Shape: Mean Invariant Moment 1 | 4.196E-02 | 6.477E-01 | 1.026E-01 | 1.052E-01 | -2.293 |
| CA | Haralick: Std. Deviation Information Measure 2 | 4.338E-02 | 1.446 | 1.207E-01 | 1.099E-01 | 9.369 |

FIG. 15

| Cohort | Feature Name | P Value | Haz. Ratio | BCR Mean | NR Mean | % Diff. |
|---|---|---|---|---|---|---|
| AA+CA | Sub-Graph: Number Isolated Nodes | 3.026E-05 | 1.941 | 2.143E-01 | 7.059E-02 | 1.01E+02 |
| AA+CA | Shape: Min / Max Fourier Descriptor 4 | 1.232E-03 | 6.268E-01 | -1.122 | -1.050 | 6.61 |
| AA+CA | Delaunay: Triangle Area Std. Deviation | 1.755E-03 | 1.524 | 3.095E+01 | 2.263E+01 | 3.10E+01 |
| AA+CA | Delaunay: Triangle Area Disorder | 5.609E-03 | 1.622 | 6.611E-01 | 6.435E-01 | 2.69 |
| AA+CA | Shape: Mean Invariant Moment 4 | 6.037E-03 | 6.019E-01 | 1.653E-05 | 1.817E-05 | -9.44 |
| AA+CA | Shape: Mean Fractal Dimension | 1.092E-02 | 1.633 | 2.480E-01 | 2.432E-01 | 2.30 |
| AA+CA | CGT: Std. Deviation Tensor Contrast Entropy | 1.171E-02 | 1.364 | 9.053E-03 | 2.386E-03 | 1.17E+02 |
| AA+CA | Shape: Mean Invariant Moment 1 | 1.175E-02 | 6.762E-01 | 1.027E-01 | 1.046E-01 | -1.83 |
| AA+CA | Sub-Graph: Number Central Nodes | 1.845E-02 | 1.291 | 1.086 | 1.012 | 7.92 |
| AA+CA | Shape: Median Fourier Descriptor 4 | 1.853E-02 | 7.686E-01 | -1.562E-08 | -8.570E-08 | 1.79E+02 |
| AA+CA | Haralick: Mean Correlation | 2.063E-02 | 6.941E-01 | -1.683E-01 | -1.500E-01 | 1.16E+01 |
| AA+CA | CGT: Range Tensor Energy | 2.358E-02 | 1.293 | 3.512E-02 | 9.824E-03 | 1.13E+02 |
| AA+CA | Shape: Median Fractal Dimension | 2.558E-02 | 1.461 | 2.219E-01 | 2.165E-01 | 2.48 |
| AA+CA | CGT: Std. Deviation Tensor Intensity Variance | 3.151E-02 | 1.279 | 6.353E-02 | 1.866E-02 | 1.09E+02 |
| AA+CA | Shape: Mean Distance Ratio | 3.407E-02 | 1.427 | 5.849E-01 | 5.558E-01 | 1.62 |

FIG. 16

POPULATION-SPECIFIC PREDICTION OF PROSTATE CANCER RECURRENCE BASED ON STROMAL MORPHOLOGY FEATURES

CROSS REFERENCE TO RELATED APPLICATIONS

This application claims the benefit of U.S. Provisional Patent Application No. 62/879,711 filed Jul. 29, 2019, entitled "STROMAL IMAGE FEATURES DERIVED FROM HEMATOXYLIN AND EOSIN (H&E) IMAGES OF PROSTATE CANCER STROMA FOR PREDICTION OF BIOCHEMICAL RECURRENCE FREE SURVIVAL FOLLOWING RADICAL PROSTATECTOMY", the contents of which are herein incorporated by reference in their entirety.

FEDERAL FUNDING NOTICE

This invention was made with government support under the grant(s) CA199374, CA202752, CA208236, CA216579, CA220581, CA239055, and RR012463, awarded by the National Institutes of Health; and grant(s) W8IXWH-15-1-0558, W8IXWH-16-1-0329, and W8IXWH-18-1-0440 awarded by the Department of Defense; and grant(s) DGE1451075 awarded by the National Science Foundation; and grant(s) IBX004121A awarded by the United States Department of Veterans Affairs. The government has certain rights in the invention.

BACKGROUND

Prostate cancer (PCa) has the highest incidence of any cancer among males in the United States. Surgical resection of the prostate (radical prostatectomy, RP) is prescribed as a curative therapy for approximately 75,000 newly diagnosed patients each year. 30-40% of patients experience biochemical recurrence (BCR) following RP. Clinical decisions about the prescription of adjuvant therapy are made based on estimates of the probability of cancer recurrence following surgery for PCa patients.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 7 illustrates a table showing selected demographic, clinical, and pathologic features of the entire patient dataset of the example use case, in connection with various aspects discussed herein.

FIG. 8 illustrates a table showing a comparison of HR with 95% CI and p value of the ENC model trained on AA patients with various clinical models, in connection with various embodiments discussed herein.

FIG. 9 illustrates a table showing the results of classification experiments (in terms of AUC, HR, 95% CI for the HR, and p) for each training and validation cohort combination of the example use case, in connection with various embodiments discussed herein.

FIG. 10 illustrates a table showing comparison of Area Under Receiver Operating Characteristic Curve (AUC), Hazard Ratio (HR) between predicted high and low risk groups, 95% confidence interval (CI) for the HR, and p value comparisons between the Kattan and CAPRA-S nomograms and one of the classifiers trained in the example use case, in connection with various aspects discussed herein.

FIG. 11 illustrates a table showing the features selected for the two models for AA patients in the example use case, in connection with various aspects discussed herein.

FIG. 12 illustrates a table showing association of stromal image features with tumor biomarkers, with Pearson Correlation Coefficient (PCC) and associated p value, in connection with various embodiments discussed herein.

FIG. 13 illustrates a table showing the feature classes of the 242 QH features of the example use case, in connection with various embodiments discussed herein.

FIG. 14 illustrates a table showing descriptors that were identified as prognostic (via Cox proportional hazards regression) of Biochemical Recurrence-Free Survival (BRFS) in the AA only ($V_{T,AA}$) subdivision of the 127-patient training cohort, in connection with various aspects discussed herein.

FIG. 15 illustrates a table showing descriptors that were identified as prognostic (via Cox proportional hazards regression) of Biochemical Recurrence-Free Survival (BRFS) in the CA only ($V_{T,CA}$) subdivision of the 127-patient training cohort, in connection with various aspects discussed herein.

FIG. 16 illustrates a table showing descriptors that were identified as prognostic (via Cox proportional hazards regression) of Biochemical Recurrence-Free Survival (BRFS) in the AA+CA ($V_{T,AA+CA}$) combined group of the 127-patient training cohort, in connection with various aspects discussed herein.

DETAILED DESCRIPTION

Figure 1:
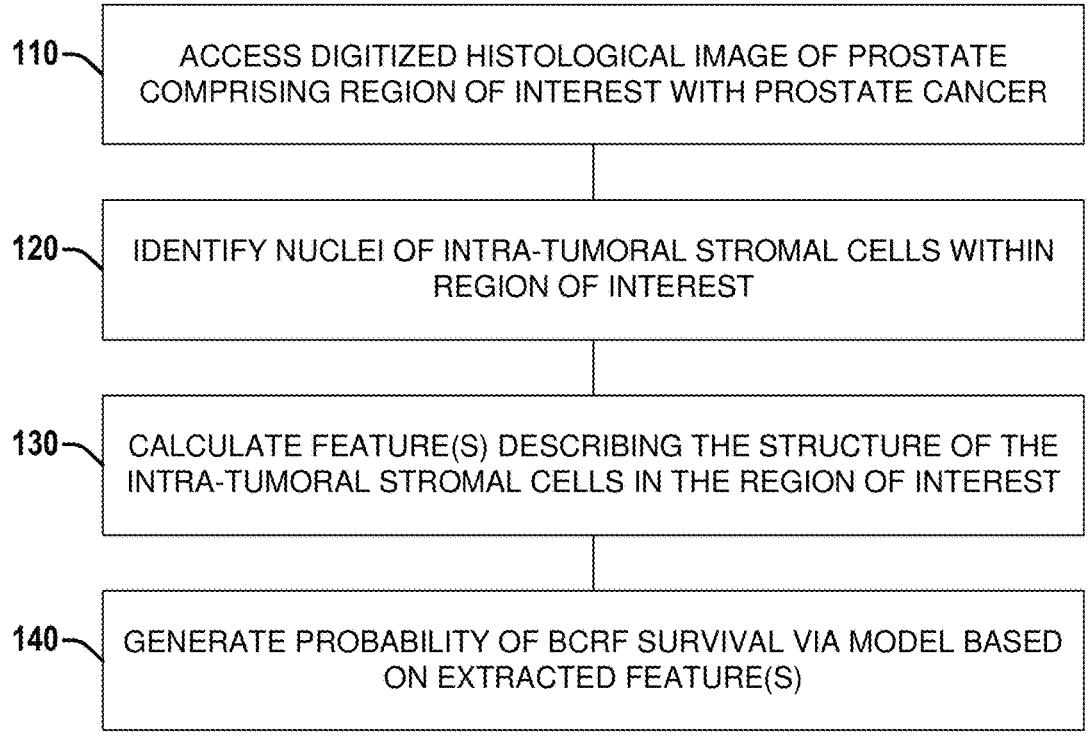
FIG. 1 illustrates a flow diagram of an example method/set of operations that can be performed by one or more processors to determine a probability of prostate cancer recurrence free-survival for a patient based on quantitative histomorphometric (QH) features of intra-tumoral stroma of prostate cancer from that patient, according to various aspects discussed herein.

Various embodiments discussed herein can comprise techniques that can facilitate determination of a risk of recurrence of prostate cancer, which can be in the form of a probability of prostate cancer recurrence-free survival, or a risk score associated with prostate cancer for the patient, depending on the embodiment. Risk determination can be based on morphological features of intra-tumoral stroma via a model trained on those morphological features.

In some population sub-groups, prostate cancer progression, response to certain therapies, and/or probability or risk of recurrence can be (at least on average) more similar between members of those population sub-groups than between members of that sub-group compared with one or more other sub-groups and/or than within the population at large. In various embodiments, the model employed can be trained on intra-tumoral stroma morphological features for a specific population sub-group, and can determine risk for a patient who is a member of that population sub-group.

Techniques discussed herein can be employed by various embodiments to one or more of: (a) determine a probability of prostate cancer recurrence-free survival for a patient based on intra-tumoral stromal morphological features, (b) determine a risk score associated with prostate cancer for a patient based on intra-tumoral stromal morphological features, or (c) train a classifier to facilitate one or more of (a) or (b). The techniques discussed herein comprise techniques that facilitate: (1) identification of nuclei of intra-tumoral stroma in a region of interest of a stained histology slide; (2) generation of one or more quantitative histomorphometric (QH) features of the stromal morphology from the region of interest; (3) determining a probability of prostate cancer recurrence-free survival or a risk score associated with prostate cancer for a patient based on the QH feature(s) via a model trained on those QH feature(s) (e.g., and optionally for a population sub-group comprising the patient); (4) determining one or more best QH features that are the most prognostic of biochemical recurrence and/or recurrence-free survival; and (5) constructing a model to determine a probability of prostate cancer recurrence-free survival and/or a risk score associated with prostate cancer based on the best QH feature(s). Each of these techniques and others are discussed in greater detail below, along with example application of specific techniques in connection with a use case, although the specific techniques employed can vary, depending on the embodiment.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Referring to FIG. 1, illustrated is a flow diagram of an example method/set of operations 100 that can be performed by one or more processors to determine a probability of prostate cancer recurrence free-survival for a patient based on quantitative histomorphometric (QH) features of intra-tumoral stroma of prostate cancer from that patient, according to various aspects discussed herein. Processor(s) can include any combination of general-purpose processors and dedicated processors (e.g., graphics processors, application processors, etc.). The one or more processors can be coupled with and/or can include memory or storage and can be configured to execute instructions stored in the memory or storage to enable various apparatus, applications, or operating systems to perform the operations. The memory or storage devices may include main memory, disk storage, or any suitable combination thereof. The memory or storage devices can comprise—but is not limited to—any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 can comprise, at 110, accessing a digitized histological image of a prostate of a patient. The image can comprise a region of interest that comprises prostate cancer and intra-tumoral stroma. In various embodiments and in the example use case discussed below, the image volume can be obtained via a system and/or apparatus implementing the set of operations 100, or can be obtained from a separate medical imaging system. Additionally, the image volume can be accessed contemporaneously with or at any point prior to performing the set of operations 100.

The set of operations 100 can further comprise, at 120, identifying nuclei of intra-tumoral stromal cells within the region of interest, according to techniques discussed herein. For example, a first deep learning model can be employed to identify nuclei within the region of interest, and a second deep learning model can be employed to identify intra-tumoral stroma within the region of interest. Based on the locations of nuclei and intra-tumoral stroma in the region of interest, the locations of nuclei of intra-tumoral stroma can be determined.

The set of operations 100 can further comprise, at 130, calculating one or more features describing the structure of the intra-tumoral stromal cells from the region of interest. The extracted features can comprise any of the quantitative histomorphometric (QH) features discussed herein, and can be features determined to be prognostic in determining a probability of prostate cancer recurrence-free survival.

The set of operations 100 can further comprise, at 140, generating a probability of prostate cancer recurrence-free survival based on the one or more extracted features via a trained model. In some embodiments, the model can be trained based on a training set of patients from a population sub-group that comprises the patient from whom the digitized histological slide was obtained.

Additionally or alternatively, set of operations 100 can comprise one or more other actions discussed herein in connection with determining a probability of prostate cancer recurrence-free survival based on intra-tumoral stromal morphological features.

Figure 2:
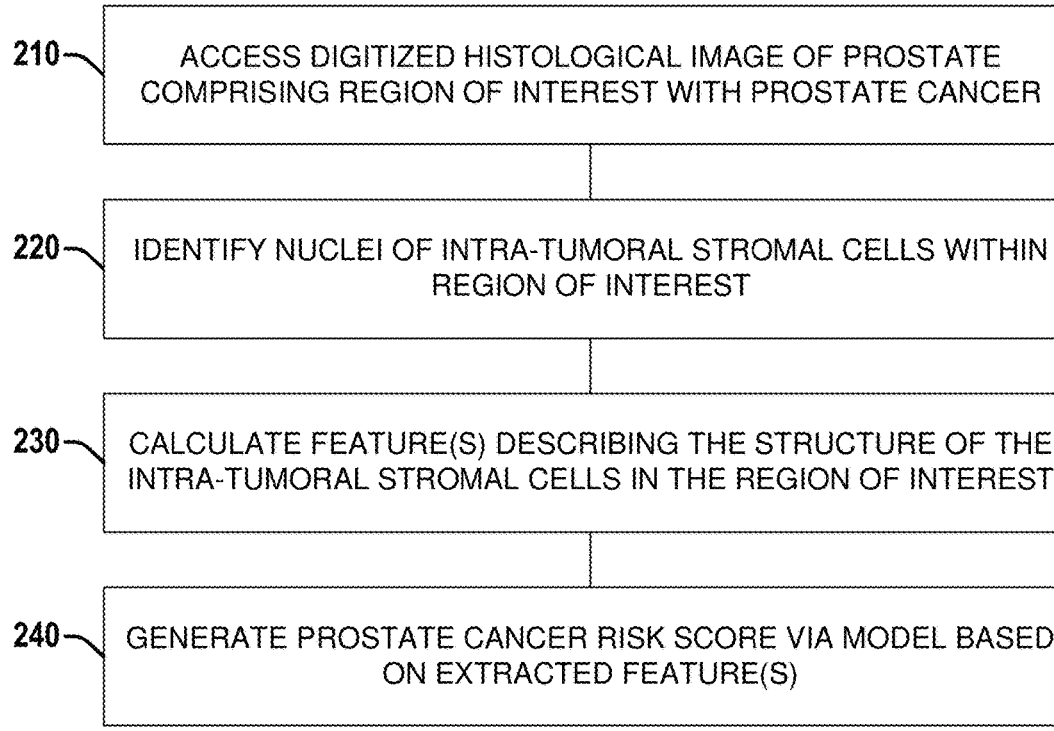
FIG. 2 illustrates a flow diagram of an example method/set of operations that can be performed by one or more processors to determine a risk score associated with prostate cancer for a patient based on QH features of intra-tumoral stroma of prostate cancer from that patient, according to various aspects discussed herein.

Referring to FIG. 2, illustrated is a flow diagram of an example method/set of operations 200 that can be performed by one or more processors to determine a risk score associated with prostate cancer for a patient based on QH features of intra-tumoral stroma of prostate cancer from that patient, according to various aspects discussed herein.

The set of operations 200 can comprise, at 210, accessing a digitized histological image of a prostate of a patient. The image can comprise a region of interest that comprises prostate cancer and intra-tumoral stroma. In various embodiments and in the example use case discussed below, the image volume can be obtained via a system and/or apparatus implementing the set of operations 200, or can be obtained from a separate medical imaging system. Additionally, the image volume can be accessed contemporaneously with or at any point prior to performing the set of operations 200.

The set of operations 200 can further comprise, at 220, identifying nuclei of intra-tumoral stromal cells within the region of interest, according to techniques discussed herein. For example, a first deep learning model can be employed to identify nuclei within the region of interest, and a second deep learning model can be employed to identify intra-tumoral stroma within the region of interest. Based on the locations of nuclei and intra-tumoral stroma in the region of interest, the locations of nuclei of intra-tumoral stroma can be determined.

The set of operations 200 can further comprise, at 230, calculating one or more features describing the structure of the intra-tumoral stromal cells from the region of interest. The extracted features can comprise any of the quantitative histomorphometric (QH) features discussed herein, and can be features determined to be prognostic in determining a risk score associated with prostate cancer.

The set of operations 200 can further comprise, at 240, generating a risk score associated with prostate cancer based on the one or more extracted features via a trained model. In some embodiments, the model can be trained based on a training set of patients from a population sub-group that comprises the patient from whom the digitized histological slide was obtained.

Additionally or alternatively, set of operations 200 can comprise one or more other actions discussed herein in connection with determining a risk score associated with prostate cancer based on intra-tumoral stromal morphological features.

Figure 3:
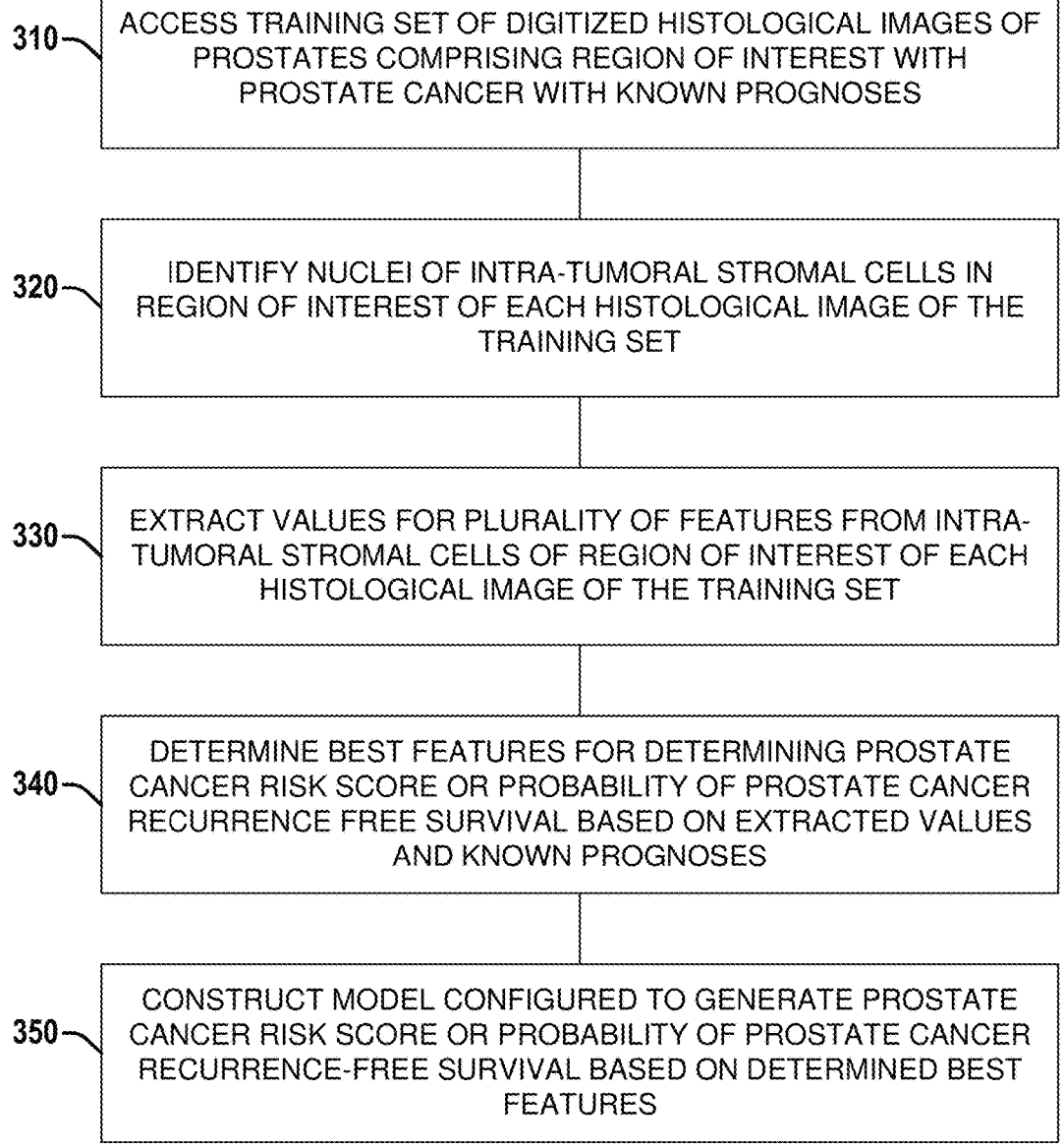
FIG. 3 illustrates a flow diagram of an example method/set of operations that can be performed by one or more processors to train a model to determine responsiveness one of a probability of prostate cancer recurrence-free survival or a risk score associated with prostate cancer based on QH features of intra-tumoral stroma in prostate cancer, according to various aspects discussed herein.

Referring to FIG. 3, illustrated is a flow diagram of an example method/set of operations 300 that can be performed by one or more processors to train a model to determine responsiveness one of a probability of prostate cancer recurrence-free survival or a risk score associated with prostate cancer based on QH features of intra-tumoral stroma in prostate cancer, according to various aspects discussed herein.

The set of operations 300 can comprise, at 310, accessing a training set of digitized histological slides, each of which is associated with a distinct patient and has a region of interest comprising prostate cancer. Each of the images in the training set can be associated with a known prognosis (e.g., biochemical recurrence positive or biochemical recurrence negative). In some embodiments, each image of the training set can be from a patient that is a member of a population sub-group.

The set of operations 300 can further comprise, at 320, for each image of the training set, identifying nuclei of intra-tumoral stromal cells within the region of interest of that image, according to techniques discussed herein. For example, a first deep learning model can be employed to identify nuclei within the region of interest, and a second deep learning model can be employed to identify intra-tumoral stroma within the region of interest. Based on the locations of nuclei and intra-tumoral stroma in the region of interest, the locations of nuclei of intra-tumoral stroma can be determined.

The set of operations 300 can further comprise, at 330, for each image of the training set, extracting associated values for a plurality of features describing the structure of the intra-tumoral stromal cells from the region of interest of that image. The extracted features can comprise any of the quantitative histomorphometric (QH) features discussed herein, and can be features determined to be prognostic in determining a risk score associated with prostate cancer.

The set of operations 300 can further comprise, at 340, determining one or more best features for one of determining a probability of prostate cancer recurrence-free survival or determining a prostate cancer risk score. The best features can be determined based on the extracted values for the images of the training set and the associated known prognoses, using techniques discussed herein.

The set of operations 300 can further comprise, at 350, constructing a model (e.g., a machine learning model, an elastic-net penalized Cox regression model, etc.) configured to determine one of a probability of prostate cancer recurrence-free survival or a prostate cancer risk score, based on the determined one or more best features.

Additionally or alternatively, set of operations 300 can comprise one or more other actions discussed herein in connection with constructing a model to determine a probability of prostate cancer recurrence-free survival or a risk score associated with prostate cancer for a patient based on intra-tumoral stromal morphological features.

Additional aspects and embodiments are discussed below in connection with the following example use case.

Example Use Case: Deep Learning Derived Signature of Stromal Morphology is Prognostic of Prostate Cancer Recurrence Following Prostatectomy in African American Patients The following discussion provides example embodiments in connection with an example use case involving determination of probability of prostate cancer recurrence-free survival or a risk score associated with prostate cancer based on model(s) trained on intra-tumoral stromal morphological features for particular population sub-groups.

A. Overview

Figure 4:
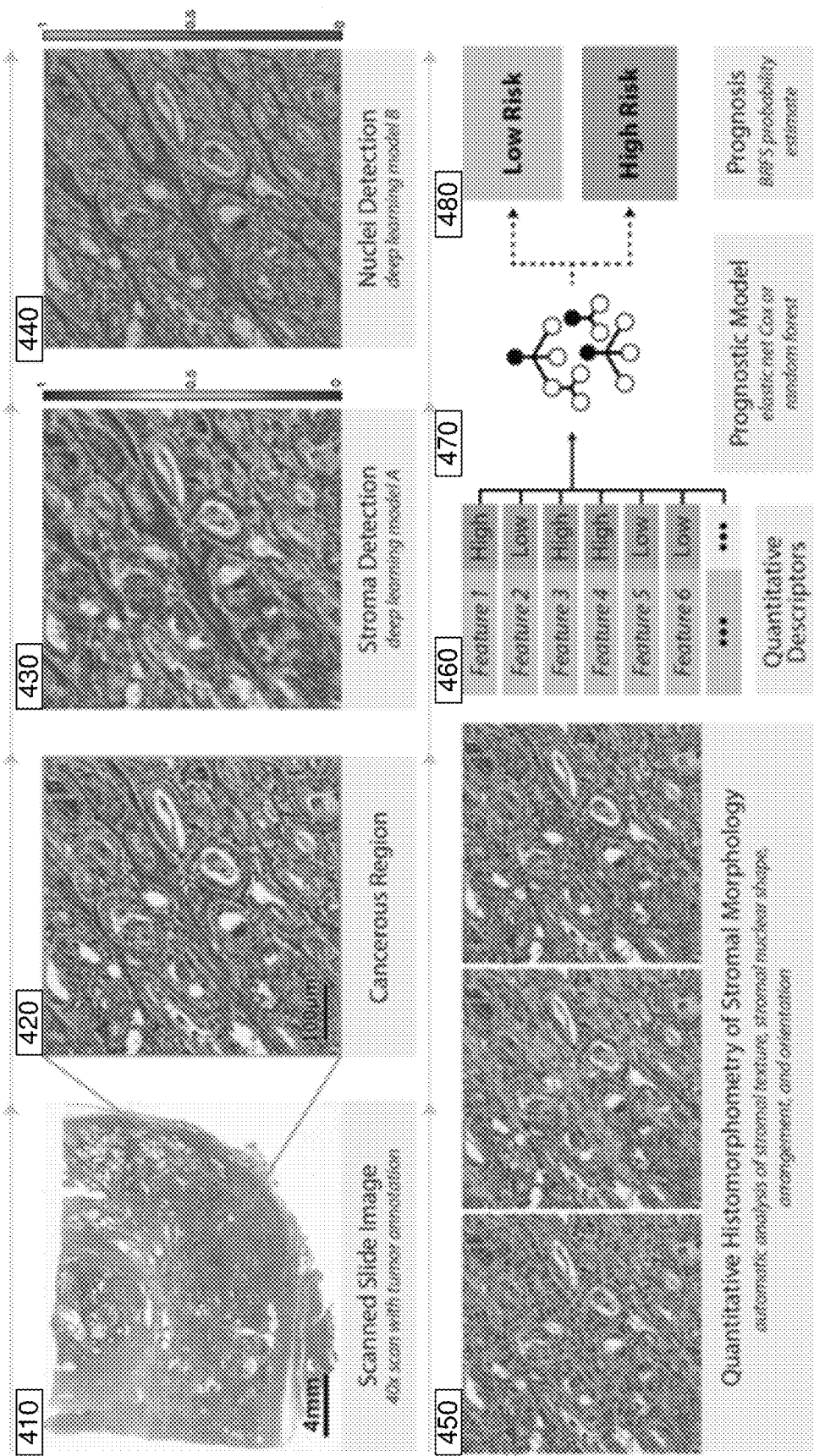
FIG. 4 illustrates a series of example images and diagrams showing an overview of the techniques employed in the example use case, in connection with various embodiments discussed herein.
Figure 5:
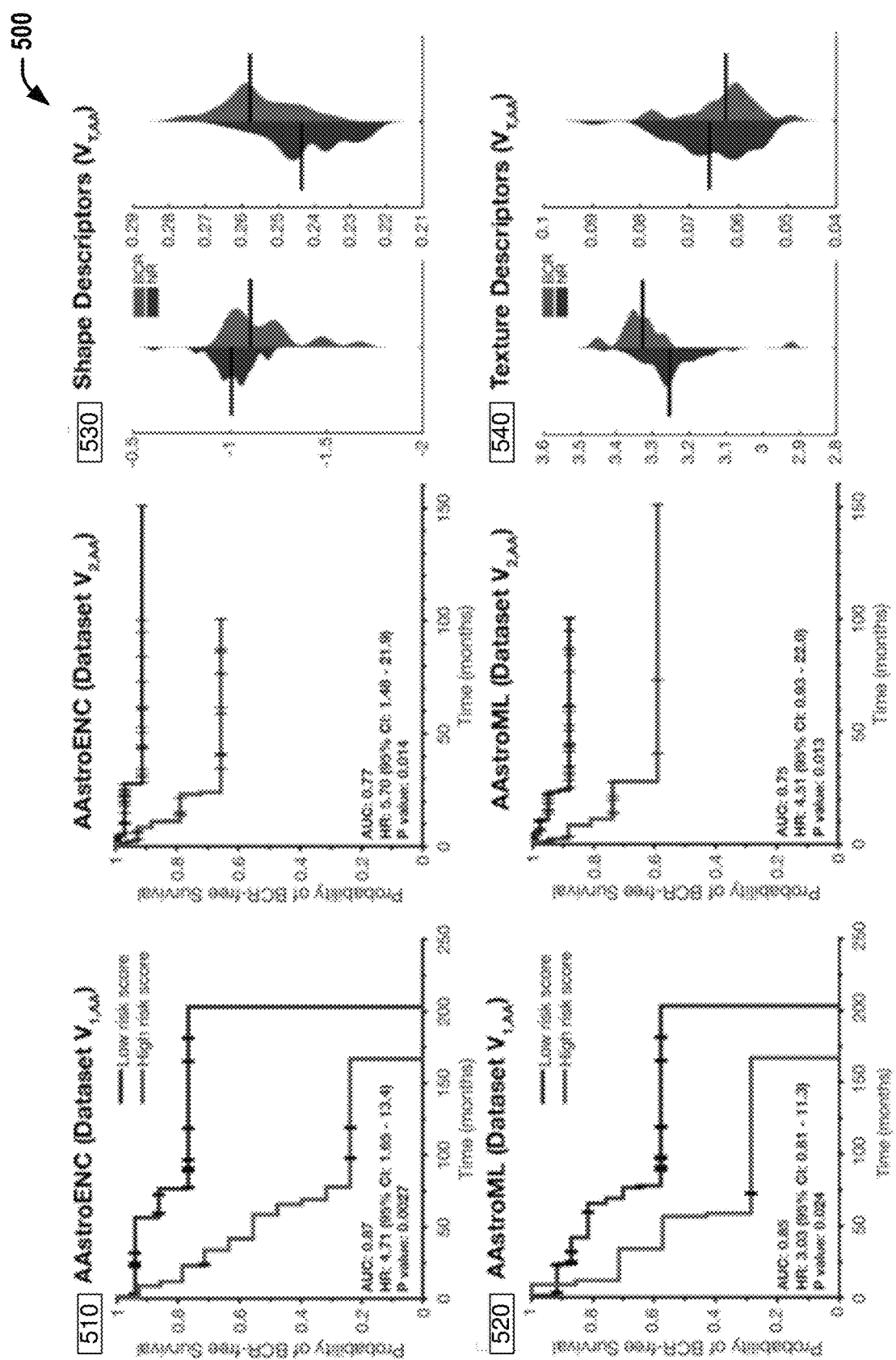
FIG. 5 illustrates Kaplan-Meier survival curve estimates for a machine learning model and an elastic-net penalized Cox regression (ENC) model trained on African American (AA) patients on the two held out AA datasets, along with the distributions of QH descriptors of stromal nuclear shape and texture used by these models, in connection with various aspects discussed herein.
Figure 6:
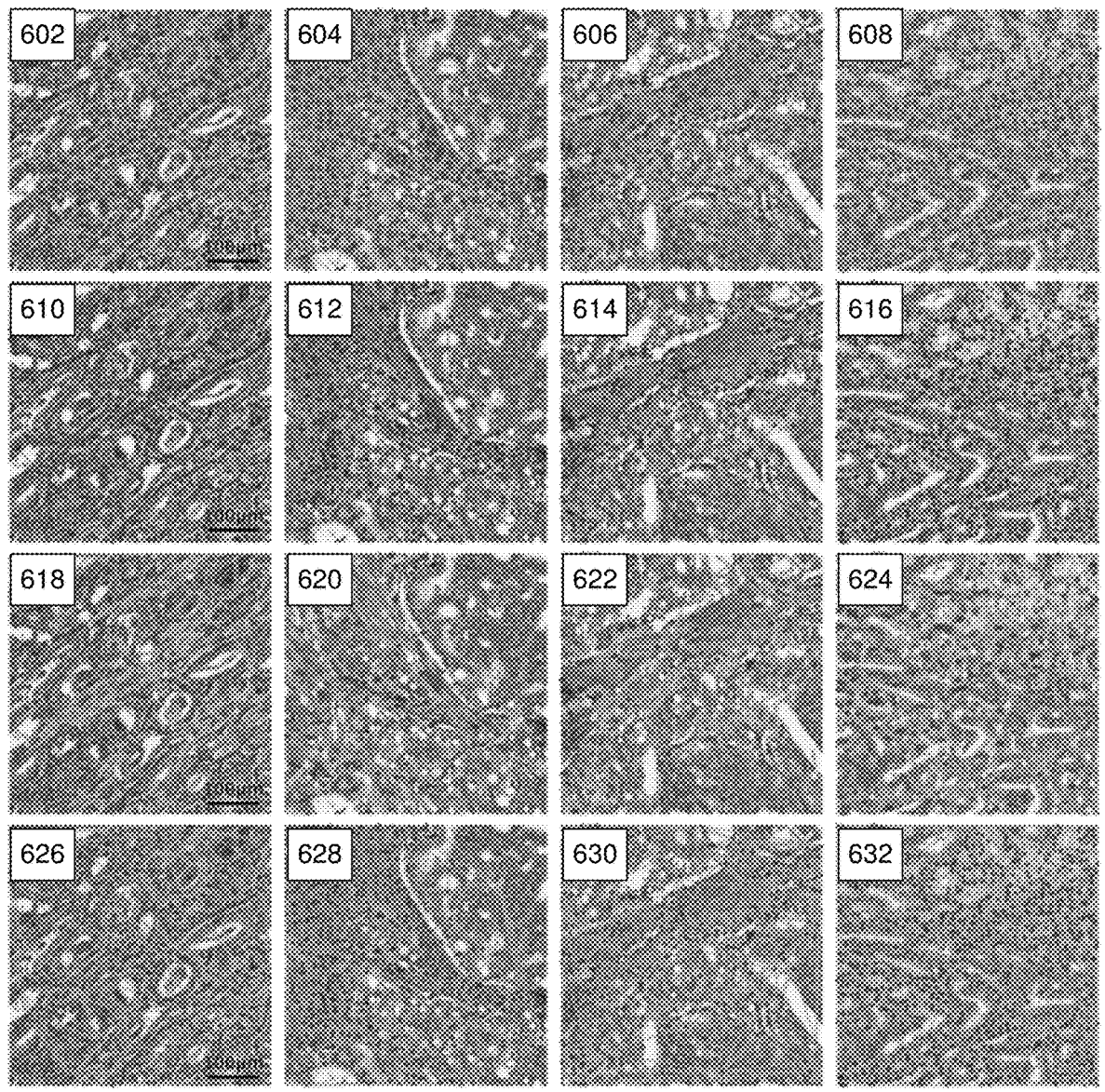
FIG. 6 illustrates example patient samples showing example stromal morphology features visualized for AA and CA high- and low-risk cases, in connection with various embodiments discussed herein.

Approximately 30-40% of prostate cancer (PCa) patients experience disease recurrence following radical prostatectomy (RP). Existing models for recurrence risk prediction do not take into account patient race or details of tumor morphology, despite evidence that African American (AA) patients experience more aggressive disease than Caucasian Americans (CA). The example use case used deep learning based algorithms to compute quantitative descriptors of stromal morphology. It was found that these descriptors differ between AA and CA patients, and that these metrics can be used to create population-specific PCa recurrence risk prediction models for AA patients that outperformed population nonspecific models, including the current clinical standards, in validation on two external datasets (total n=209) consisting of patients gathered from three institutions. FIGS. 4-6 show example images and graphs in connection with the example use case, and FIGS. 7-16 show tables of example data and other information in connection with the example use case.

B. Discussion

Prostate cancer (PCa) has the highest incidence of any cancer among males in the United States. Surgical resection of the prostate (radical prostatectomy, RP) is prescribed as a curative therapy for approximately 75,000 newly diagnosed patients each year. 30-40% of patients experience biochemical recurrence (BCR) following RP. Clinical decisions about the prescription of adjuvant therapy are made based on estimates of the probability of cancer recurrence following surgery for PCa patients.

Increasing evidence suggests that African-Americans (AA) have a higher likelihood of being diagnosed with PCa and may experience more aggressive disease. Compared to Caucasian-American (CA) males, AA men have a 1.76-fold higher lifetime probability of developing PCa, and a 2.20-fold greater chance of disease-related death. Recent investigations at the genomic, epigenomic, transcriptomic, and proteomic levels have suggested significant differences in the biology of AA versus CA tumors.

Numerous studies have demonstrated a role for the stroma in the pathogenesis of a number of cancers, showing changes in stromal cell phenotypes and extracellular matrix (ECM) composition, and the presence of biomarkers similar to those observed during wound repair. Despite these findings, stromal morphology is not explicitly considered by pathologists in PCa recurrence risk estimation.

The example use case presents a deep learning based quantitative histomorphometry method for recurrence risk prognosis in AA patients using measurements relating to morphology of intra-tumoral stroma. The algorithm employed in the example use case used deep learning models to segment nuclei and stroma in 334 whole-mount RP histopathology images, followed by the calculation of 242 quantitative descriptors of stromal morphology. These features described the shape, orientation, and arrangement of nuclei within the stroma as well as the texture of the stroma.

Referring to FIG. 6, illustrated are example patient samples showing example stromal morphology features visualized for AA and CA high- and low-risk cases, in connection with various embodiments discussed herein. In FIG. 4, the first column (602, 610, 618, and 626) shows features computed for the AA high-risk group (AA-Biochemical Recurrence Positive (BCR+)) example patient, the second column (604, 612, 620, and 628) shows features computed for the AA low-risk group (AA-BCR Negative (BCR−)) example patient, the third column (606, 614, 622, and 630) shows features computed for the CA high-risk group (CA-BCR+) example patient, and the fourth column (608, 616, 624, and 632) shows features computed for the CA low-risk group (CA-BCR−) example patient. The first row (602-608) shows Voronoi diagrams, the second row (610-616) shows minimal spanning trees, the third row (618-624) shows directionality colormaps, and the fourth row (626-632) shows global graphs, each for stromal nuclei in the relevant AA/CA high-/low-risk group example patient for that column.

Referring to FIG. 14, illustrated is a table showing descriptors that were identified as prognostic (via Cox proportional hazards regression) of Biochemical Recurrence-Free Survival (BRFS) in the AA only ($V_{T,AA}$) subdivision of the 127-patient training cohort, in connection with various aspects discussed herein. Referring to FIG. 15, illustrated is a table showing descriptors that were identified as prognostic (via Cox proportional hazards regression) of Biochemical Recurrence-Free Survival (BRFS) in the CA only ($V_{T,CA}$) subdivision of the 127-patient training cohort, in connection with various aspects discussed herein. Referring to FIG. 16, illustrated is a table showing descriptors that were identified as prognostic (via Cox proportional hazards regression) of Biochemical Recurrence-Free Survival (BRFS) in the AA+CA ($V_{T,AA+CA}$) combined group of the 127-patient training cohort, in connection with various aspects discussed herein.

Machine learning (ML) and Elastic net-penalized Cox regression (also referred to herein as elastic net Cox or ENC) based classifiers were trained using the stromal image features to estimate recurrence likelihood following RP. These models were validated using two independent holdout datasets $V_1$ (n=64) and $V_2$ (n=145), with results shown in FIGS. 5 and 9, and discussed in greater detail below. The performance of these models was compared to that of current clinical standards for postoperative risk prognosis, namely the Kattan and CAPRA-S nomograms. When tested against the independent holdout validation sets, the models created for the example use case were found to outperform existing nomograms in biochemical recurrence free survival (BRFS) prognosis in $V_{1,AA}$ and $V_{2,AA}$. Referring to FIG. 10, illustrated is a table showing comparison of Area Under Receiver Operating Characteristic Curve (AUC), Hazard Ratio (HR) between predicted high and low risk groups, 95% confidence interval (CI) for the HR, and p value comparisons between the Kattan and CAPRA-S nomograms and one of the classifiers trained in the example use case, in connection with various aspects discussed herein.

Referring to FIG. 4, illustrated is a series of example images and diagrams showing an overview of the techniques employed in the example use case, in connection with various embodiments discussed herein. Paraffin-embedded, resected prostate glands were sectioned using a microtome. H&E slides were then prepared and digitally scanned (410). For each slide, a single representative cancerous region was annotated on the digital image by a pathologist (indicated via the line in 410, and magnified view in 420). Stroma and nuclei were then segmented from the region of interest by deep learning models, yielding class probability maps in 430 and 440. These probability maps were thresholded and used to compute stromal image features, as in the examples at 450 and as shown at 460. Stromal morphology descriptors were used to train prognostic models (indicated at 470), which estimate biochemical recurrence risk probability (indicated at 480).

In the example use case, no stroma-based ML or ENC model with any training set ($V_{T,AA}$, $V_{T,CA}$, or $V_{T,AA+CA}$) was prognostic of disease recurrence for the CA or AA+CA cohorts in more than one validation set (log-rank p value>0.05). However, both the ML and ENC models trained on AA patients (referred to herein, respectively, as AAstroML and AAstroENC) were successful in estimating recurrence risk for AA patients in both validation datasets. Referring to FIG. 9, illustrated is a table showing the results of classification experiments (in terms of AUC, HR, 95% CI for the HR, and p) for each training and validation cohort combination of the example use case, in connection with various embodiments discussed herein. In FIG. 9, statistically significant results are indicated in bold. Referring to FIG. 5, illustrated are Kaplan-Meier survival curve estimates for the AAstroML and AAstroENC models on the two held out AA datasets, along with the distributions of QH descriptors of stromal nuclear shape and texture used by these models, in connection with various aspects discussed herein. In FIG. 5, Kaplan-Meier survival curve estimates of predicted low versus high BRFS risk groups in $V_{1,AA}$ and $V_{2,AA}$ are shown for AAstroENC at 510 and for AAstroML at 520. Distributions in $V_{T,AA}$ of QH descriptors of stromal nuclear shape (e.g., min/max Fourier descriptor 4 and mean fractal dimension) features used by AAstro models are shown at 530, and stromal texture (mean Haralick information measure 1 and mean contrast inverse moment) features used by AAstro models are shown at 540.

The best performing model for AA patients, AAstroENC, was an ENC model trained on ten descriptors of stromal morphology. Referring to FIG. 11, illustrated is a table showing the features selected for the two models for AA patients in the example use case, in connection with various aspects discussed herein. The features selected for AAstro-ENC included descriptors of stromal texture, and nuclear shape and arrangement. AAstroENC achieved an AUC of 0.87 and hazard ratio of 4.71 (95% CI: 1.65-13.4, p=0.0027) in $V_{1,AA}$, and AUC of 0.77 and hazard ratio of 5.7 (95% CI: 1.48-21.90, p=0.014) in $V_{2,AA}$, outperforming AAstroML in both datasets.

In a multivariable Cox regression analysis, AAstroENC was prognostic in both $V_{1,AA}$ (HR=2.80; 95% CI=1.15-6.85; p=0.024) and $V_{2,AA}$ (HR=2.36; 95% CI=1.38-4.06; p=0.002) when adjusted for routine clinical and pathological variables used in existing risk estimation models. Referring to FIG. 8, illustrated is a table showing a comparison of HR with 95% CI and p value of the AAstroENC model with various clinical models, in connection with various embodiments discussed herein. The only other variable retaining a significant HR in both validation datasets when adjusting for other variables and AAstroENC score was presence of seminal vesicle invasion (SVI).

AAstroENC and AAstroML outperformed clinical models in both validation datasets. The only nomogram experiment that achieved a statistically significant hazard ratio was the Kattan nomogram applied to $V_{1,AA}$. In this case, however, the nomogram model achieved a hazard ratio of only 2.67, compared with 4.71 for AAstroENC. The performance of models created using CAPRA-S and Kattan nomograms is provided in FIG. 10, discussed above.

The prognostic utility of stromal features observed in the example use case adds to a growing base of knowledge implicating tissue regions not traditionally examined by pathologists as harboring prognostic clues. In a study involving more than 6000 image features derived from breast cancer images, one group identified stromal image features as being more strongly prognostic of survival than tumor epithelial features. Similarly, another group showed that computer extracted descriptors of nuclear morphology, derived from benign, tumor-adjacent regions was strongly associated with the likelihood of biochemical recurrence post-surgery. Collectively, these findings reinforce the importance of interrogating patterns within the stroma and tumor-adjacent regions on histopathology.

The example use case did not create prognostic models for CA patients based on stromal features; though this may have been possible with a larger training dataset. In addition, some patients initially considered in the study were lost during follow up. Additionally, BCR prognosis models trained on CA patients failed to effectively stratify BCR risk in CA men. It is possible that the poor model performance on the CA cohort was in part due to increased diversity and/or genetic heterogeneity within these groups, and possible that sub-division into smaller population sub-groups with less diversity and/or genetic heterogeneity could provide improved results. Finally, the example use case did not consider features within the tumor epithelium, and it is possible that embodiments combining stromal and epithelial features will yield even better risk estimation models.

However, the example use case was the first to show the role of stromal features in PCa BCR likelihood estimation, and is the first QH study to assess population-specific differences in PCa. In addition, the findings of the example use case provide some biological insight into differences in PCa morphology between AA and CA patients. Various embodiments can reproduce and/or validate these findings on larger and/or different cohorts, and/or analyze stromal features in the context of features from additional tissue compartments, as well as biopsies from multifocal disease.

C. Methods

Datasets and Sample Preparation

A total of 334 prostate cancer patients who underwent radical prostatectomy were identified for inclusion within the study of the example use case. The surgical procedures and sample preparation were conducted at three different institutions. Resected prostates were fixed overnight in formalin, serially sectioned, and entirely submitted in quadrants. Hematoxylin- and Eosin-stained (H&E) slides were prepared using the formalin-fixed, paraffin-embedded tissue (FFPE). Each case was reviewed by a pathologist to select a single representative slide. The slides were then scanned using a whole-slide scanner. The images were reviewed by a pathologist, and a single representative cancerous region was digitally annotated in each image. This annotated region was used for the quantitative histomorphometry experiments in this study. An example annotation is shown in FIG. 4 at 410.

The patients were divided into three cohorts: $V_T$ (training, n=127), $V_1$ (validation 1, n=62), and $V_2$ (validation 2, n=145). $V_T$ was used for feature discovery and model training, and $V_1$ and $V_2$ were used for independent holdout validation of prognostic model performance. All datasets were approximately class balanced between AA and CA patients. $V_T$ and $V_1$ were also approximately class balanced with respect to patients who experienced BCR versus those who did not. Referring to FIG. 7, illustrated is a table showing selected demographic, clinical, and pathologic features of the entire patient dataset of the example use case, in connection with various aspects discussed herein.

$V_T$ (n=127) and $V_1$ (n=62) comprised samples collected at the Hospital of the University of Pennsylvania. The slides corresponding to these samples were scanned at 40× magnification using an Aperio Scanscope whole-slide scanner (Leica, Wetzlar, Germany) at the University of Pennsylvania Department of Pathology. $V_2$ consisted of samples collected at University Hospitals Cleveland Medical Center (UHCMC) (n=70) and at New York Presbyterian Weill Cornell Medical Center (NYP) (n=75). Samples prepared at UHCMC were scanned at 40× magnification on a Zeiss Axio Scan.Z1 slide scanning microscope (Zeiss, Oberkochen, Germany). The samples prepared at NYP were scanned at 40× magnification using an Aperio Scanscope whole-slide scanner (Leica, Wetzlar, Germany) at the Weill Cornell Medicine Department of Pathology and Laboratory Medicine. Examples of digitized H&E slide images from the example use case are shown in FIG. 4 at 410-420.

Nuclear Detection and Segmentation

Nuclei were segmented using a deep learning method developed based on convolutional neural networks. The output of this deep learning model was a probability map that indicates the likelihood that each pixel in the image is part of a nucleus (e.g., as shown at FIG. 4 at 440). A threshold was determined by inspection of image data from $V_T$ and applied in conjunction with maximum and minimum size thresholds to convert the probability map to a binary matrix. Closed shapes corresponding to nuclear borders were traced from this binary map to yield the final matrix of nuclear boundary coordinates.

Stromal Detection and Segmentation

The intra-tumoral stroma was segmented using a deep learning model based on U-Net convolutional neural networks. The output of this deep learning model was a probability map representing the likelihood that each pixel in the image was part of the stromal compartment (e.g., as shown at FIG. 4 at 430). A threshold for this map was determined by visual inspection of image data from $V_T$ and comparison with annotated stroma. This information was combined with the coordinates of nuclei in the images to determine the coordinates of stromal nuclei.

Feature Extraction

Using the boundary coordinates of stromal nuclei and of the stromal compartment (the output of the segmentation process), 242 QH features were calculated for each patient. The extracted features included metrics derived from the stromal texture, the connectivity graph of stromal nuclei, nuclear centroids, descriptors of nuclear shape and orientation, and sub-graph features. Referring to FIG. 13, illustrated is a table showing the feature classes of the 242 QH features of the example use case, in connection with various embodiments discussed herein. Visualizations of selected stromal image feature calculations are shown in FIG. 6 for patients from each race and BCR status combination.

Statistical Methods and Definitions

Biochemical recurrence-free survival (BRFS) was measured from the date of surgery to the date of biochemical recurrence which was defined as at least two prostate specific antigen (PSA) test results greater than 0.2 ng/mL. Patients who did not experience BCR were right-censored at the date of last follow-up in survival analyses.

Within each racial subset of $V_T$ ($V_{T,AA}$, $V_{T,CA}$, and $V_{T,AA+CA}$), all possible combinations of features were tested for correlation by calculating the Pearson correlation coefficient (PCC). In order to remove redundant features (e.g., features that were almost linearly dependent upon one another), the feature with smaller absolute β value was removed from pairs of features that had PCC greater than 0.90. Referring to FIG. 12, illustrated is a table showing association of stromal image features with tumor biomarkers, with PCC and associated p value, in connection with various embodiments discussed herein.

ENC models were built using a modified version of Glmnet for Matlab.

AUC (area under the receiver operating characteristic curve) values were calculated for each model based on binary endpoints (BCR or non-BCR). AUC describes the integral of the ratio of true versus false positives as the classification decision threshold is varied; an AUC value of 0.5 would indicate random guessing in a binary classification problem.

Cox proportional hazards regression was used to assess the significance and magnitude of differences in survival between the high and low BCR risk classes predicted by the models.

In order to determine whether the models of the example use case were prognostic of risk independent of clinical and pathological variables, multivariable Cox proportional hazards regression models were implemented. These regression models were fitted to the risk score of the models to be analyzed, as well as selected clinical and pathological predictors. In order to facilitate comparison of features with different units, z-scores were calculated for each feature value and were used as inputs for the Cox proportional hazards regression models.

All statistical tests were 2-sided, and were performed with the significance level set at 0.05. All statistical and feature analyses were conducted using MATLAB (The Mathworks, Inc., Natick, Massachusetts, United States) and Python 3 (Python Software Foundation, https://www.python.org/).

Identification of Stromal Nuclear Features Prognostic of BCR

The prognostic capability of each stromal image feature with respect to BRFS was assessed in $V_T$ using univariate Cox proportional hazards regression to determine which features might be suitable for risk prognosis model construction. Cox proportional hazards regression models were fit to each stromal feature within each population subset ($V_{T,AA}$, $V_{T,CA}$, and $V_{T,AA+CA}$) to assess the degree and significance of prognostic potential within each racial group.

BCR Prognosis Model Construction using Stromal Image Features

Machine learning and Elastic Net Cox models were constructed to estimate BCR risk using stromal image feature values. These models take a patient's image feature values as input, and output an estimate of the recurrence risk probability of the patient.

For the machine learning models, combinations of classifiers (support vector machines (SVM), random forests (RF), naïve Bayes, linear discriminant analysis (LDA), and quadratic discriminant analysis (QDA)) and numbers of features (1-25) were tested for optimal performance over 10 iterations of 3-fold cross validation in $V_T$. The hyperparameters that produced the highest statistically significant Cox proportional hazards regression hazard ratio were identified for each training cohort ($V_{T,AA}$, $V_{T,CA}$, $V_{T,AA+CA}$). Following model parameter optimization using the training set, models were locked down and tested against $V_1$ and $V_2$. For each validation experiment, AUC values were calculated, Kaplan-Meier survival curves constructed, and single variable Cox proportional hazards regression applied to determine hazard ratio and P value.

Elastic net-penalized Cox proportional hazards regression (elastic net Cox; ENC) was implemented to model recurrence risk based on the quantitative histomorphometry features. These models were fit to the survival data. Elastic net regularization linearly combines the $L_1$ and $L_2$ penalties of the lasso and ridge regularization operators. The elastic net mixing parameter α and shrinkage parameter λ were optimized in the training set using three-fold cross validation. α was optimized for maximal hazard ratio, and λ for minimum deviance. To determine the optimal risk score threshold for stratifying high recurrence risk from low recurrence risk patients, the example used case employed the following algorithm: (1) risk scores were calculated for each patient in the training set using the ENC model, (2) risk scores between the 20th and 80th percentiles were retained as candidate thresholds (in various embodiments, other thresholds can be employed instead), (3) each candidate was tested as a threshold in the training set and log-rank p values and hazard ratios were calculated, (4) candidate thresholds with statistically significant performance were retained, and the value corresponding to the largest hazard ratio was selected. ENC models were validated by calculating risk scores in the validation datasets and grouping patients into high- and low-risk groups by comparing risk score to the optimized threshold. Following parameter optimization and threshold determination, model parameters were locked down and the models were tested against the holdout validation sets $V_1$ and $V_2$. Analysis of validation set performance was performed using the same method as described for the machine learning models.

Comparison of QH-Based Models with Clinical Variables and Nomograms

To determine whether the best model, AAstroENC, was independent of clinical variables, multivariable Cox Proportional Hazards Models were fit using the model score as well as clinical and pathological variables. The variables compared were age at the time of surgery, Gleason score, preoperative PSA value, presence of seminal vesicle invasion (SVI), presence of extracapsular extension (ECE), and surgical margin status.

In order to assess the performance of the AAstro model relative to the clinical gold standard, two postoperative recurrence risk prognosis nomograms were implemented, CAPRA-S and Kattan. The Kattan nomogram was implemented with the most up-to-date model parameters retrieved from the Memorial Sloan-Kettering Cancer Center (MSKCC) website (accessed May, 2019), and both nomograms were implemented with t=5-year prediction targets. Classification models were created from the nomograms by thresholding the nomogram output probabilities at a recurrence risk probability value of 0.5. In addition, Kaplan-Meier and Cox proportional hazards analyses were performed on the output of these nomogram-based classifiers for each cohort to evaluate the differences in outcomes for the predicted low risk and high-risk classes.

ADDITIONAL EMBODIMENTS

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, 300, 400 or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein relate to training and/or employing classifiers to generate a probability of prostate cancer recurrence-free survival or a prostate cancer risk score based on morphological features of intra-tumoral stroma that are not perceivable by the human eye, and involve computation that cannot be practically performed in the human mind. As one example, machine learning and/or deep learning classifiers as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then be used and applied to create desired results more accurately, more consistently, and with greater reliability than existing approaches, thereby producing the technical effect of improving the performance of the machine, computer, or system with which embodiments are implemented.

Figure 17:
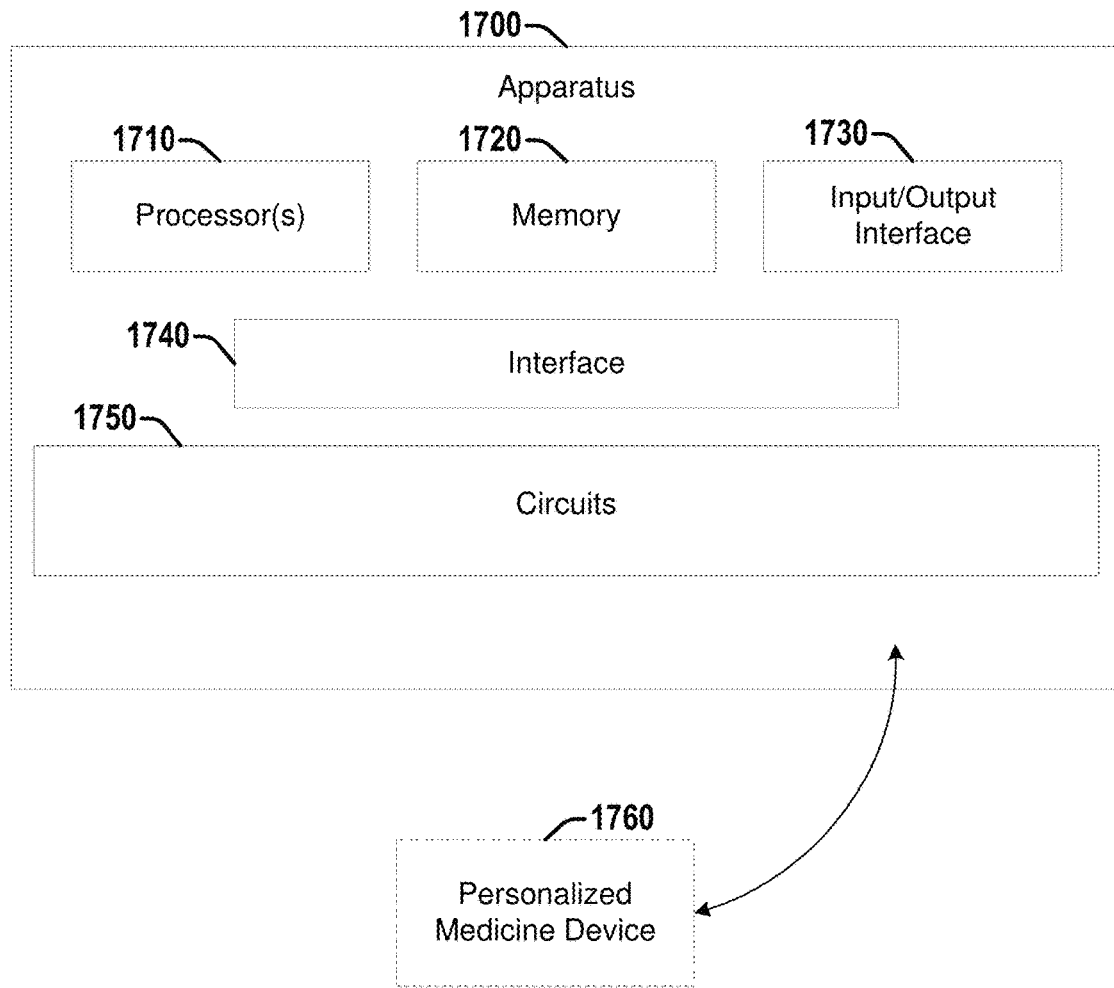
FIG. 17 illustrates a diagram of an example apparatus that can facilitate determination of a probability of prostate cancer recurrence free-survival or a risk score associated with prostate cancer for a patient stromal morphology of prostate cancer from that patient and/or training a machine learning (ML) classifier or ENC model to perform such determination, according to various embodiments discussed herein.

Referring to FIG. 17, illustrated is a diagram of an example apparatus 1700 that can facilitate determination of a probability of prostate cancer recurrence free-survival or a risk score associated with prostate cancer for a patient stromal morphology of prostate cancer from that patient and/or training a machine learning (ML) classifier or ENC model to perform such determination, according to various embodiments discussed herein. Apparatus 1700 can be configured to perform various techniques discussed herein, for example, various operations discussed in connection with sets of operations 100, 200, 300, and/or 400. Apparatus 1700 can comprise one or more processors 1710 and memory 1720. Processor(s) 1710 can, in various embodiments, comprise circuitry such as, but not limited to, one or more single-core or multi-core processors. Processor(s) 1710 can include any combination of general-purpose processors and dedicated processors (e.g., graphics processors, application processors, etc.). The processor(s) can be coupled with and/or can comprise memory (e.g., of memory 1720) or storage and can be configured to execute instructions stored in the memory 1720 or storage to enable various apparatus, applications, or operating systems to perform operations and/or methods discussed herein. Memory 1720 can be configured to store one or more images (e.g., digitized stained histology, etc.) of prostate cancer (e.g., for training and/or prognosing). Each of the image(s) can comprise a plurality of pixels or voxels, each pixel or voxel having an associated intensity. Memory 1720 can be further configured to store additional data involved in performing operations discussed herein, such as for determining a probability of prostate cancer recurrence-free survival or a risk score associated with prostate cancer and/or training a ML or DL model to determine a probability of prostate cancer recurrence-free survival or a risk score associated with prostate cancer, as discussed in greater detail herein.

Apparatus 1700 can also comprise an input/output (I/O) interface 1730 (e.g., associated with one or more I/O devices), a set of circuits 1750, and an interface 1740 that connects the processor(s) 1710, the memory 1720, the I/O interface 1730, and the set of circuits 1750. I/O interface 1730 can be configured to transfer data between memory 1720, processor 1710, circuits 1750, and external devices, for example, a medical imaging device (e.g., microscope, whole-slide scanner, slide-scanning microscope, etc.), and/or one or more remote devices for receiving inputs and/or providing outputs to a clinician, patient, etc., such as optional personalized medicine device 1760.

The processor(s) 1710 and/or one or more circuits of the set of circuits 1750 can perform one or more acts associated with a method or set of operations discussed herein, such as set of operations 100, 200, 300, or 400. In various embodiments, different acts (e.g., different operations of a set of operations) can be performed by the same or different processor(s) 1710 and/or one or more circuits of the set of circuits 1750.

Apparatus 1700 can optionally further comprise personalized medicine device 1760. Apparatus 1700 can be configured to provide the probability of prostate cancer recurrence-free survival or a risk score associated with prostate cancer, or other data to personalized medicine device 1760. Personalized medicine device 1760 may be, for example, a computer assisted diagnosis (CADx) system or other type of personalized medicine device that can be used to facilitate monitoring and/or treatment of an associated medical condition. In some embodiments, processor(s) 1710 and/or one or more circuits of the set of circuits 1750 can be further configured to control personalized medicine device 1760 to display the determination or prediction of response to chemoradiation treatment for the patient or other data on a computer monitor, a smartphone display, a tablet display, or other displays.

Examples herein can include subject matter such as an apparatus, a microscope and/or slide-scanning system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for generating system-independent quantitative perfusion measurements, according to embodiments and examples described.

Example 1 is a non-transitory computer-readable medium storing computer-executable instructions that, when executed, cause a processor to perform operations, comprising: accessing a digitized histological image of a prostate of a patient, wherein the histological image comprises a region of interest associated with prostate cancer; identifying nuclei of intra-tumoral stromal cells within the region of interest; extracting, for the region of interest of the digitized histological image, one or more features describing the structure of the intra-tumoral stromal cells; and generating, via a model based at least on the one or more features, a probability of prostate cancer recurrence-free survival for the patient based at least on the extracted one or more features.

Example 2 comprises the subject matter of any variation of any of example(s) 1, wherein the one or more operations further comprise: segmenting nuclei within the region of interest; and segmenting intra-tumoral stroma within the region of interest, wherein identifying the nuclei of the intra-tumoral cells is based at least in part on the segmented nuclei and the segmented intra-tumoral stroma.

Example 3 comprises the subject matter of any variation of any of example(s) 2, wherein the nuclei and the intra-tumoral stroma are segmented via one or more deep learning models.

Example 4 comprises the subject matter of any variation of any of example(s) 1-3, wherein the model is based at least on the one or more features for a training set of histological images associated with a population sub-group, wherein the patient is a member of the population sub-group.

Example 5 comprises the subject matter of any variation of any of example(s) 4, wherein the population sub-group is African American.

Example 6 comprises the subject matter of any variation of any of example(s) 1-5, wherein the one or more features comprise at least one of: one or more Voronoi tessellation features, one or more Delauney triangulation features, one or more minimum spanning tree features, one or more local nuclear cluster graph features, one or more nuclear shape features, one or more cell orientation entropy features, one or more sub-graph features, or one or more texture features.

Example 7 comprises the subject matter of any variation of any of example(s) 1-6, wherein the model is a machine learning model.

Example 8 comprises the subject matter of any variation of any of example(s) 1-6, wherein the model is an elastic-net penalized Cox regression model.

Example 9 is a non-transitory computer-readable medium storing computer-executable instructions that, when executed, cause a processor to perform operations, comprising: accessing a digitized histological image of a prostate of a patient, wherein the histological image comprises a region of interest associated with prostate cancer; identifying nuclei of intra-tumoral stromal cells within the region of interest; extracting, for the region of interest of the digitized histological image, one or more features describing the structure of the intra-tumoral stromal cells; and generating, via a model based at least on the one or more features, a risk score associated with prostate cancer for the patient based at least on the extracted one or more features.

Example 10 comprises the subject matter of any variation of any of example(s) 9, wherein the one or more operations further comprise: segmenting nuclei within the region of interest; and segmenting intra-tumoral stroma within the region of interest, wherein identifying the nuclei of the intra-tumoral cells is based at least in part on the segmented nuclei and the segmented intra-tumoral stroma.

Example 11 comprises the subject matter of any variation of any of example(s) 10, wherein the nuclei and the intra-tumoral stroma are segmented via one or more deep learning models.

Example 12 comprises the subject matter of any variation of any of example(s) 9-11, wherein the model is based at least on the one or more features for a training set of histological images associated with a population sub-group, wherein the patient is a member of the population sub-group.

Example 13 comprises the subject matter of any variation of any of example(s) 12, wherein the population sub-group is African American.

Example 14 comprises the subject matter of any variation of any of example(s) 9-13, wherein the one or more features comprise at least one of: one or more Voronoi tessellation features, one or more Delauney triangulation features, one or more minimum spanning tree features, one or more local nuclear cluster graph features, one or more nuclear shape features, one or more cell orientation entropy features, one or more sub-graph features, or one or more texture features.

Example 15 comprises the subject matter of any variation of any of example(s) 9-14, wherein the model is a machine learning model.

Example 16 comprises the subject matter of any variation of any of example(s) 9-14, wherein the model is an elastic-net penalized Cox regression model.

Example 17 is a non-transitory computer-readable medium storing computer-executable instructions that, when executed, cause a processor to perform operations, comprising: accessing a training set of digitized histological images, wherein each image of the training set is of an associated prostate of an associated patient, wherein each image of the training set comprises an associated region of interest comprising prostate cancer, and wherein each image of the training set is associated with a known prognosis for the associated patient of that image; for each image of the training set: identifying nuclei of intra-tumoral stromal cells of that image in intra-tumoral stroma of that image within the region of interest of that image; and extracting, for each feature of a plurality features, an associated value for that feature for that image based at least on one or more of the stromal nuclei of that image or the intra-tumoral stroma of that image; determining one or more best features for determining one of a prostate cancer risk score or a probability of prostate-cancer recurrence-free survival from among the plurality of features, wherein the one or more best features are determined based at least on: the known prognosis for the associated patient for each image of the plurality of images and the associated value for each feature of the plurality of features for each image of the plurality of images; and constructing a model configured to generate the one of the prostate cancer risk score or the probability of prostate-cancer recurrence-free survival for an additional histological image comprising an additional prostate with prostate cancer for an additional patient based at least on the one or more best features.

Example 18 comprises the subject matter of any variation of any of example(s) 17, wherein the one or more operations further comprise: for each image of the training set: segmenting nuclei of that image within the region of interest of that image; and segmenting the intra-tumoral stroma of that image within the region of interest of that image, wherein identifying the nuclei of intra-tumoral stromal cells of that image is based at least in part on the segmented nuclei of that image and the segmented intra-tumoral stroma of that image.

Example 19 comprises the subject matter of any variation of any of example(s) 18, wherein the nuclei of each image and the intra-tumoral stroma of each image are segmented via one or more deep learning models.

Example 20 comprises the subject matter of any variation of any of example(s) 17-19, wherein the associated patient for each image of the training set is a member of a population sub-group, wherein the additional patient is a member of the population sub-group.

Example 21 comprises the subject matter of any variation of any of example(s) 20, wherein the population sub-group is African American.

Example 22 comprises the subject matter of any variation of any of example(s) 17-21, wherein the one or more best features comprise at least one of: one or more Voronoi tessellation features, one or more Delauney triangulation features, one or more minimum spanning tree features, one or more local nuclear cluster graph features, one or more nuclear shape features, one or more cell orientation entropy features, one or more sub-graph features, or one or more texture features.

Example 23 comprises the subject matter of any variation of any of example(s) 17-22, wherein the model is a machine learning model.

Example 24 comprises the subject matter of any variation of any of example(s) 17-22, wherein the model is an elastic-net penalized Cox regression model.

Example 25 comprises the subject matter of any variation of any of example(s) 17-24, wherein the one or more best features are determined based at least in part on Cox proportional hazard regression.

Example 26 comprises the subject matter of any variation of any of example(s) 17-25, wherein the one or more best features are determined based at least in part on determining Pearson correlation coefficients between pairs of features of the plurality of features.

Example 27 comprises an apparatus comprising means for executing any of the described operations of examples 1-26.

Example 28 comprises a machine readable medium that stores instructions for execution by a processor to perform any of the described operations of examples 1-26.

Example 29 comprises an apparatus comprising: a memory; and one or more processors configured to: perform any of the described operations of examples 1-26.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:
    accessing a digitized histological image of a prostate of a patient, wherein the digitized histological image comprises a region of interest associated with prostate cancer;
    generating a first probability map that indicates a likelihood that each pixel in the digitized histological image is part of a nucleus;
    determining nuclear coordinates using the first probability map;
    generating a second probability map that indicates a likelihood that each pixel in the digitized histological image is part of a stromal compartment;
    combining information from the second probability map with the nuclear coordinates to identifying nuclei of intra-tumoral stromal cells within the region of interest;
    extracting, for the region of interest of the digitized histological image, one or more features describing a structure of the intra-tumoral stromal cells; and
    generating, via a model based at least on the one or more features, a risk score associated with prostate cancer for the patient based at least on the one or more features.

2. The non-transitory computer-readable medium of claim 1, wherein the operations further comprise:
    segmenting nuclei within the region of interest; and
    segmenting intra-tumoral stroma within the region of interest,
    wherein identifying the nuclei of the intra-tumoral stromal cells is based at least in part on the segmented nuclei and the segmented intra-tumoral stroma.

3. The non-transitory computer-readable medium of claim 2, wherein the nuclei and the intra-tumoral stroma are segmented via one or more deep learning models.

4. The non-transitory computer-readable medium of claim 1, wherein the model is based at least on the one or more features for a training set of histological images associated with a population sub-group, wherein the patient is a member of the population sub-group.

5. The non-transitory computer-readable medium of claim 4, wherein the population sub-group is African American.

6. The non-transitory computer-readable medium of claim 1, wherein the one or more features comprise at least one of: one or more Voronoi tessellation features, one or more Delauney triangulation features, one or more minimum spanning tree features, one or more local nuclear cluster graph features, one or more nuclear shape features, one or more cell orientation entropy features, one or more sub-graph features, or one or more texture features.

7. The non-transitory computer-readable medium of claim 1, wherein the model is a machine learning model.

8. The non-transitory computer-readable medium of claim 1, wherein the model is an elastic-net penalized Cox regression model.

9. The non-transitory computer-readable medium of claim 1, further comprising:
    determining a likelihood of prostate cancer recurrence based upon the risk score.

10. A method of assessing prostate cancer for a patient, comprising:
    accessing an image of a prostate of a patient, wherein the image comprises a region of interest associated with prostate cancer;
    generating a first probability map that indicates a likelihood that each pixel in the image is part of a nucleus;
    determining nuclear coordinates using the first probably map;
    generating a second probability map representing a likelihood that each pixel in the image is part of a stromal compartment;
    combining information from the second probability map with the nuclear coordinates to determine coordinates of nuclei of intra-tumoral stromal cells;
    identifying boundaries of the nuclei of the intra-tumoral stromal cells and the stromal compartment within the region of interest;
    extracting, from the region of interest of the image, one or more features describing a shape, an orientation, and an arrangement of nuclei within the intra-tumoral stromal cells, wherein the boundaries of the nuclei of the intra-tumoral stromal cells and the stromal compartment are used in extracting the one or more features; and
    generating, via a model based at least on the one or more features, a risk score associated with prostate cancer for the patient.

11. The method of claim 10, further comprising:
    determining a likelihood of recurrence of the prostate cancer based upon the risk score.

12. The method of claim 10, further comprising:
    comparing the risk score to a risk score threshold to determine a likelihood of recurrence of the prostate cancer.

13. The method of claim 10, wherein the one or more features comprise metrics derived from a stromal texture, a connectivity graph of the nuclei of the intra-tumoral stromal cells, nuclear centroids, descriptors of nuclear shape and orientation, and sub-graph features.

14. The method of claim 10, further comprising:
assessing a prognostic capability of the one or more features with respect to Biochemical Recurrence-Free Survival (BRFS) using a univariate Cox proportional hazards regression.

15. The method of claim 10, wherein the one or more features further describe a shape of the intra-tumoral stromal cells, an orientation of the intra-tumoral stromal cells, and a texture of the intra-tumoral stromal cells.

16. The method of claim 10, further comprising:
segmenting nuclei of the image within the region of interest; and
segmenting the intra-tumoral stromal cells of the image within the region of interest, wherein identifying the boundaries of the nuclei of the intra-tumoral stromal cells is based at least in part on the segmented nuclei of the image and the segmented intra-tumoral stromal cells of the image.

17. The method of claim 10, wherein the one or more features are extracted after identifying the boundaries of nuclei of the intra-tumoral stromal cells and the stromal compartment within the region of interest.

18. The method of claim 10, further comprising:
segmenting nuclei using a convolutional neural network to generate the first probability map; and
segmenting the intra-tumoral stromal cells using a U-Net convolution neural network to generate the second probability map.

19. The method of claim 10, wherein the model is based at least on the one or more features associated with a population sub-group, wherein the patient is a member of the population sub-group.

20. The method of claim 19, wherein the population sub-group is African American.

21. The method of claim 10, wherein the one or more features comprise at least one of: one or more Voronoi tessellation features, one or more Delauney triangulation features, one or more minimum spanning tree features, one or more local nuclear cluster graph features, one or more nuclear shape features, one or more cell orientation entropy features, one or more sub-graph features, or one or more texture features.

22. An apparatus for assessing prostate cancer within a patient, comprising:
a memory configured to store an image of a prostate of a patient, wherein the image comprises a region of interest associated with prostate cancer;
a one or more circuits configured to:
generate a first probability map that indicates a likelihood that each pixel in the image is part of a nucleus;
determine nuclear coordinates using the first probably map;
generate a second probability map representing a likelihood that each pixel in the image is part of a stromal compartment;
combine information from the second probability map with the nuclear coordinates to determine coordinates of a nuclei of intra-tumoral stromal cells;
identify boundaries of the nuclei of the intra-tumoral stromal cells and the stromal compartment within the region of interest using convolutional neural network to represent a likelihood each pixel in the image is part of the stromal compartment;
extract, from the region of interest of the image, one or more features describing a structure of the intra-tumoral stromal cells, wherein the boundaries of the nuclei of the intra-tumoral stromal cells and the stromal compartment are used in extracting the one or more features; and
generate, via a model based at least on the one or more features, a risk score associated with prostate cancer within the patient.

23. The apparatus of claim 22, wherein the one or more features comprise metrics derived from a stromal texture, a connectivity graph of the nuclei of the intra-tumoral stromal cells, nuclear centroids, descriptors of nuclear shape and orientation, and sub-graph features.

24. The apparatus of claim 22, wherein the one or more features describe a shape of the intra-tumoral stromal cells, an orientation of the intra-tumoral stromal cells, an arrangement of the nuclei within the intra-tumoral stromal cells, and a texture of the intra-tumoral stromal cells.

25. The apparatus of claim 22, wherein the one or more circuits are further configured to extract the one or more features after identifying the boundaries of nuclei of the intra-tumoral stromal cells and the stromal compartment within the region of interest.

26. The apparatus of claim 22, wherein the one or more circuits are further configured to
determine a likelihood of recurrence of the prostate cancer based upon the risk score.

* * * * *